United States Patent [19]

Baseman

[11] Patent Number: 4,945,041

[45] Date of Patent: Jul. 31, 1990

[54] **MONOCLONAL ANTIBODIES FOR *MYCOPLASMA PNEUMONIAE* AND USE FOR DIAGNOSIS OF PNEUMONIA**

[75] Inventor: Joel B. Baseman, San Antonio, Tex.

[73] Assignee: Board of Regents

[21] Appl. No.: 4,767

[22] Filed: Jan. 9, 1987

Related U.S. Application Data

[63] Continuation of Ser. No. 552,822, Nov. 17, 1983, abandoned.

[51] Int. Cl.$^5$ ........................ G01N 33/53; C12N 5/00; C12P 21/00
[52] U.S. Cl. .................................... 435/7; 435/70.21; 435/172.2; 435/240.26; 435/240.27; 435/948; 436/528; 436/529; 436/548; 530/387; 530/808; 530/809; 935/89; 935/93; 935/95; 935/106
[58] Field of Search ................. 424/85; 435/68, 172.2, 435/243, 948, 7, 240.26, 240.27; 530/387, 808, 809; 935/89, 93, 95, 106; 436/528, 529, 548

[56] References Cited

U.S. PATENT DOCUMENTS

| | | | |
|---|---|---|---|
| 4,196,265 | 4/1980 | Koprowski et al. | 425/2 |
| 4,361,509 | 11/1982 | Zimmerman et al. | 530/413 |
| 4,504,585 | 3/1985 | Reynolds | 436/528 X |

FOREIGN PATENT DOCUMENTS 0056309  5/1978  Japan .................................... 436/529

OTHER PUBLICATIONS

Hu, Ping C., et al., "Demonstration of Antibodies to *Mycoplasma Pneumoniae* Attachment Protein in Human Sera and Respiratory Secretions", vol. 41, No. 1, Infection and Immunity, Jul. 1983, pp. 437–439.
Krause, Duncan C., et al., "Inhibition of *Mycoplasma pneumoniae* Hemadsorption and Adherence to Respiratory Epithelium by Antibodies to a Membrane Protein", vol. 39, No. 3, Infection and Immunity, Mar. 1983, pp. 1180–1186.
Leith, Debra K., et al., "Hemadsorption and Virulence are Separable Properties of *Mycoplasma pneumoniae*", vol. 39, No. 2, Infection and Immunity, Feb. 1983, pp. 844–850.
Krause, Duncan C., et al., "Reacquisition of Specific Proteins Confers Virulence in *Mycoplasma pneumoniae*", vol. 39, No. 2, Infection and Immunity, Feb. 1983, pp. 830–836.
Lieth, Debra K., et al., "Host Discrimination of *Mycoplasma pneumoniae* Proteinaceous Immunogens", vol. 157, Journal of Experimental Medicine, Feb. 1983, pp. 502–514.
Baseman, J. B., et al., "Molecular Basis for Cytadsorption of *Mycoplasma pneumoniae*", vol. 151, No. 3, Journal of Bacteriology, Sep. 1982, pp. 1514–1522.
Krause, Duncan C., et al., "*Mycoplasma pneumoniae* Proteins That Selectively Bind to Host Cells", vol. 37, No. 1, Infection and Immunity, Jul. 1982, pp. 382–386.
Krause, Duncan C., et al., "Identification of *Mycoplasma pneumoniae* Proteins Associated with Hemadsorption and Virulence", vol. 35, No. 3, Infection and Immunity, Mar. 1982, pp. 809–817.
Hansen, Eric J., et al., "Isolation of Mutants of *Mycoplasma pneumoniae* Defective in Hemadsorption", vol. 23, No. 3, Infection and Immunity, Mar. 1979, pp. 903–906.
Hu, Ping C., et al., "Surface Parasitism by *Mycoplasma Pneumoniae* of Respiratory Epithelium", vol. 145, The Journal of Experimental Medicine, 1977, pp. 1328–1343.
Hansen, Eric J., et al, "Detection of Antibody-Accessible Proteins on the Cell Surface of *Haemophilus influenzae* Type b", vol. 33, No. 3, Infection and Immunity, Sep. 1981, pp. 950–953.
Hu, P. C., et al, "Mycoplasma pneumoniae Infection: Role of a Surface Protein in the Attachment Organelle", Science, vol. 216, Apr. 1982, pp. 313–315.
Morrison-Plummer, et al, An ELISA to Detect Monoclonal Antibodies Specific for Lipid Determinants of *Mycoplasma pneumoniae*, Journal of Immunological Methods, 64 (1983), pp. 165–178.
Feldner, et al., Nature, vol. 298, (1982), pp. 765–766.
Indiveri, et al., J. Immunol. Meth., vol. 39, (1980), pp. 343–354.
Sevier et al., Clin. Chem., vol. 27, No. 11, (1981), pp. 1797–1806.

*Primary Examiner*—Esther M. Kepplinger
*Attorney, Agent, or Firm*—John W. Schneller; William M. Blackstone

[57] ABSTRACT

Monoclonal antibodies specific for *Mycoplasma pneumoniae* determinants and their use in the diagnosis of mycoplasma pneumoniae and purification of a protein determinant of *M. pneumoniae*.

11 Claims, No Drawings

MONOCLONAL ANTIBODIES FOR *MYCOPLASMA PNEUMONIAE* AND USE FOR DIAGNOSIS OF PNEUMONIA

This is a continuation of application Serial No. 552,822 filed Nov. 17, 1983, abandoned.

BACKGROUND OF THE INVENTION

This invention relates to monoclonal antibodies specific for *Mycoplasma pneumoniae*. More specifically, this invention involves hybridomas which produce monoclonal antibodies specific for *M. pneumoniae* antigens and their use for purification of *M. pneumoniae* protein antigens and in a diagnostic test.

*Mycoplasma pneumoniae*, a microorganism which colonizes the mucosal surface of the respiratory tract, causes primary atypical pneumonia in children and young adults. The symptoms of the disease are relatively mild and current diagnostic methods are suboptimal, consequently the incidence of the disease is probably underestimated. Infection with *M. pneumoniae* is often accompanied by the appearance of cold agglutinins in the patient's serum, a rise in complement fixation (CF) titer, and the production of antibody that inhibits the metabolic processes of the pathogen.

The most commonly used serological diagnostic test for *M. pneumoniae* is an assay for increased CF titer that uses a lipid hapten extracted from the organism as the target antigen. However, lipids are rarely good immunogens unless complexed to protein. Because of the relative unreliability of the CF assay for *M. pneumoniae*, there is a need for diagnostic methods which allow more accurate monitoring and diagnosis of this disease.

SUMMARY OF THE INVENTION

The present invention is directed to the hybridomas formed by fusion of antibody-producing cells from animals immunized with *M. pneumoniae* and a myeloma cell line which produce monoclonal antibodies specific for *M. pneumoniae* antigens. It also provides monoclonal antibodies specific for *M. pneumoniae* antigens which are produced by the hybridomas formed by the fusion of a myeloma cell line with antibody-producing cells from animals immunized with *M. pneumoniae*.

The invention is also directed to a method for producing monoclonal antibodies against a non-immunodominant antigen of a microorganism which involves the systemic administration of a microorganism to an animal followed, after an appropriate period of time, by the systemic administration of one or more doses of a mutant of that microorganism in which a mutation has been selectively induced to provide a mutant deficient in its ability to produce an immunodominant antigen, the recovery of antibody-producing cells from the immunized animal, the fusion of those antibody-producing cells with a myeloma cell line to form a hybridoma and the recovery of the monoclonal antibodies produced by that hybridoma.

The present invention is also directed to a method for the purification of *M. pneumoniae* protein P1 which involves providing a monoclonal antibody having specificity for *M. pneumoniae* protein P1, said monoclonal antibody being bound to an insoluble support system, contacting said supported monoclonal antibody with either a soluble preparation of *M. pneumoniae* or body fluid from a mammal infected with *M. pneumoniae*, and recovering substantially pure *M. pneumoniae* protein P1 from said insoluble support system.

The invention also provides reliable methods for immunochemical analysis and diagnosis of mycoplasma infection in mammals. In particular, a method is provided which involves the quantification of the amount of material immunologically bound to the monoclonal antibodies produced by a hybridoma formed by the fusion of a myeloma cell line with an antibody-producing cell from an animal immunized with *M. pneumoniae* when the monoclonal antibodies are contacted with a body fluid from a mammal. The use of the monoclonal antibodies in this manner permits a precise immunochemical analysis of mycoplasma infection. In the present application many microorganisms are described as (ATCC XXXX) where the XXXX symbolizes an accession code number of the American Type Culture Collection, Rockville, Md. All such organisms will be available to the public without restriction when a patent is granted claiming or describing these organisms.

The present invention may be better understood by reference to the Applicant's presently preferred embodiments, described in the following detailed description.

DETAILED DESCRIPTION OF THE PREFERRED EMBODIMENTS

Virulent *Mycoplasma pneumoniae* characteristically attach themselves to host tracheal and other respiratory epithelial cells as a pathogenic mechanism in the production of atypical pneumonia. Applicant has implicated a number of mycoplasma cell surface proteins, including those designated P1, P2 and HMW3 (molecular weights 165,000, 100,000 and 140,000, respectively) which play important roles in the attachment of *M. pneumoniae* to respiratory epithelium (see D. C. Krause and J. B. Baseman, "Mycoplasma pneumoniae Proteins that Selectively Bind to Host Cells." *Inf. Immun.*, vol. 37, no. 1 (July, 1982), pp. 382–386, hereby incorporated by reference). Protein P1 is apparently the major protein adhesin, but the presence of antibodies against either P1 or P2 in the host appears to be an indicator of the presence of virulent *M. pneumoniae*, and therefore, the disease.

Recognizing these surface proteins as major components in the immune response to mycoplasma infection was an important step leading to the development of the present invention. The role of these proteins in the attachment of *M. pneumoniae* to tracheal cells makes possible the use of monoclonal antibodies specific for these proteins to screen for the presence of these surface proteins as reliable indicators of mycoplasma infection. To provide a screening system for detection of these protein antigens, a series of monoclonal antibodies against these protein antigens was developed as follows.

Animals were injected with whole, virulent *M. pneumoniae* on a specific immunization protocol, and the antibody-producing cells of the immunized animal were fused with a myeloma cell line to produce a series of hybridoma cell lines with the capacity to produce monoclonal antibodies specific for *M. pneumoniae*. Recognizing the apparent role of these other surface proteins, additional monoclonal antibodies were obtained that were specific for proteins other than P1. This additional specificity was obtained by the use of an immunization protocol involving the administration of mutant *M. pneumoniae* and the subsequent fusion of antibody-producing cells from the animal immunized with the mutant *M. pneumoniae* with a myeloma cell line. Cloned hybridomas were then injected intraperitoneally in animals, the resulting tumor ascites fluid was tapped and the monoclonal antibodies purified.

During the analysis of the monoclonal antibodies secreted by the hybridomas produced by fusion of antibody-producing cells from animals immunized with both mutant and wild-type *M. pneumoniae*, clones were found secreting antibodies which were highly reactive in a whole cell enzyme-linked immunosorbent assay (ELISA) using *M. pneumoniae* organisms as antigens, yet non-reactive to the protein determinants of *M. pneumoniae*, such as P1, when tested by radioimmunoprecipitation (RIP) combined with sodium dodecylsulfate-polyacrylamide gel electrophoresis (SDS-PAGE) and autoradiography-fluorography. Surprisingly, further analysis showed that these hybridomas were producing monoclonal antibodies specific against determinants located on mycoplasma lipids.

The discovery that these monoclonal antibodies were specific for lipid antigens of *M. pneumoniae* provides another level of specificity which, when combined with the monoclonal antibodies specific for protein antigens of *M. pneumoniae* into a diagnostic method for the detection of mycoplasma infection, makes possible a highly reliable and reproducible test for the monitoring of the immune response to the presence of *M. pneumoniae* in a mammalian host. On the basis of experimentation conducted by Applicant (see Hu, P. C., A. M. Collier and J. B. Baseman, "Surface Parasitism by *Mycoplasma pneumoniae* of Respiratory Epithelium," *J. Exp. Med.*, vol. 145 (1977), pp. 1328–1343; Krause, D. C. and J. B. Baseman, "*Mycoplasma pneumoniae* Proteins that Selectively Bind to Host Cells," *Inf. Immun.*, vol. 37, no. 1 (July 1982), pp. 382–386; Baseman, J. B., R. M. Cole, D. C. Krause and D. K. Leith, "Molecular Basis for Cytadsorption of *Mycoplasma pneumoniae*," *J. Bacteriol.*, vol. 151, no. 3 (September 1982), pp. 1514–1522; each of which is hereby incorporated by reference), it is expected that the detection of surface adhesin P1 in a sample of a body fluid (primarily human serum or sputum) from an individual would provide a reliable indicator of whether that particular individual carried an *M. pneumoniae* infection. In addition to the apparent reliability of the presence of P1 as an indicator of mycoplasma pneumonia, additional reliability was conferred upon this diagnostic method by screening for the presence of other *M. pneumoniae* protein antigens such as surface adhesin P2 and/or other proteins and/or the lipid antigens of *M. pneumoniae* with monoclonals specific for determinants located on these antigens.

Screening for more than one determinant with the monoclonal antibodies of the present invention has the advantage of providing a built-in cross-check on the results of the diagnostic method, making such methods more reliable than the CF assay currently utilized for diagnosis of primary atypical pneumonia. It also allows for quantification of the antigenic load. Further, it has been found that the use of monoclonal antibodies specific for various *M. pneumoniae* determinants allows for a more precise immunochemical analysis of the immune response to mycoplasma infection because the immune response is detected at a time earlier in its development than it would have been detected by CF assay (assuming that it would have been detected by CF assay).

The present invention may be better understood by reference to the following, non-limiting examples. The *M. pneumoniae* strains used in carrying out these examples were the virulent hemadsorbing-positive ($HA^+$) M129-B15, M129-B16 and M129-B25C strains, and the spontaneously derived non-hemadsorbing ($HA^-$) class IV mutant (ATCC 39505) described by Krause, D. C., Debra K. Leith, R. M. Wilson and J. B. Baseman, "Identification of *Mycoplasma pneumoniae* Proteins Associated with Hemadsorption and Virulence," *Inf. Immun.*, vol. 35, no. 3 (March, 1982), pp. 809–817, hereby incorporated by reference.

Briefly, nitrosoguanidine-derived mutants were grouped into classes, based upon their protein content as analyzed by polyacrylamide disc-gel electrophoresis. The class IV ($HA^-$) mutant was the only mutant found to lack protein P1. Methods for the induction of mutations in *M. pneumoniae* are also discussed in Hansen, E. J., R. M. Wilson and J. B. Baseman, "Isolation of Mutants of *Mycoplasma pneumoniae* Defective in Hemadsorption," *Int. Immun.*, vol. 23, no. 3 (March 1979), pp. 903–906, hereby incorporated by reference. Briefly, the virulent M129 strain of *M. pneumoniae* was grown in Hayflick medium at 37° C. (Lipman, et al. (1969) Proc. Soc. Exp. Biol. Med. Vol. 131 pp. 1163–1167). Glass-attached organisms were exposed to N-methyl-N'-nitro-N-nitrosoguanidine at a final concentration of 25 micro g/ml in pH 6.7 phosphate-buffered saline for 30 min., which resulted in 95% mortality among the exposed cells. The mycoplasmas were then rinsed three times with pH 7.2 phosphate-buffered saline and scraped into 10 ml of Hayflick broth. A small portion (0.2 ml) of this suspension was incubated in fresh Hayflock broth for 96 h, at which time glass-adherent organisms were scraped into the spent growth medium. Serial dilutions of these cells were plated on PPLO agar plates (Lipman, et al. (1969)) and incubated at 37° C. for 8 days.

Hemadsorption-negative colonies were identified essentially by the method of Sobeslavsky, et al. (Sobeslavsky, et al. (1968) J. Bacterial V. 96, pp. 695–706). The use of a Glarex optical projection screen (Carl Zeiss, 7082 Oberkochen, West Germany) coupled to a Zeiss WL microscope greatly facilitated the identification of hemadsorption-negative colonies, because it permitted rapid viewing of large numbers of the extremely minute mycoplasma colonies for their hemadsorption characteristics. Tentative hemadsorption-negative mutants were purified by three successive applications of a single-colony isolation method involving suspension of the selected colony in broth, followed by filtration through a 0.45-mm filter, and subsequent serial dilution and plating of the filtrate.

Hemadsorption-negative mutants were isolated from independent mutagenesis experiments. These mutants were identified as *M. pneumoniae* by the use of specific antisera and by their characteristic beta-hemolysis on agar plates overlaid with sheep erythrocytes. Mycoplasmas were grown at 37° C. in 32 oz. glass prescription bottles containing 70 ml Hayflick medium at 37° C. (Hayflick, L., "Tissue Cultures and Mycoplasmas." *Tex. Rep. Biol. Med.*, vol. 23 (Suppl. 1), (1965), pp. 285–303). Exponentially growing mycoplasmas were harvested at 48–72 hours post-innoculation. Following several washes with phosphate-buffered saline (PBS), pH 7.2, *M. pneumoniae* were collected in PBS by gently scraping the glass-attached mycoplasmas and centrifuging at 10,000×g for 15 minutes.

For intrinsic labeling of *M. pneumoniae* with [$^{35}S$]-methionine, log-phase cultures were washed with PBS and pulsed for six hours at 37° C. with 250/mCi of L-[$^{35}S$]-methionine (Amersham Corp., Arlington Heights, Ill., specific activity, 1,050-1,400 Ci/mmol) in Hanks balanced salts solution containing 10% dialyzed horse serum. Cultures were washed with PBS containing 1 mM cold methionine, chased for 1.5 hours at 37° C. in Hayflick medium, then washed four times with PBS containing 1 mM cold methionine prior to collection.

EXAMPLE I. Preparation and Purification of Monoclonal Antibodies

Monoclonal antibodies against *M. pneumoniae* antigens were produced using a variation of the fusion procedure of Oi, V. T. and L. A. Herzenberg, In: B. B. Mishell and S. M. Shiigi, eds., *Selected Methods in Cellular Immunology* (San Francisco, W. H. Freeman and Company, 1980), p. 351, hereby incorporated by reference, as follows.

A. Preparation of Mouse Splenocytes For Fusion

Two different immunization protocols were established to obtain immune spleen cells for hybridoma fusions. The first protocol involved the intraperitoneal (i.p.) injection of BALB/c female mice (3-6 weeks) with 50 $\mu$g wild-type virulent *M. pneumoniae* strain B16 in saline on days 1 and 15 The humoral immune response of the mice was monitored by ELISA and RIP. Three days prior to fusion, a mouse demonstrating a strong immune response was injected i.p. with 400 $\mu$g *M. pneumoniae* B16. In the second immunization protocol, 200 $\mu$g of *M. pneumoniae* B16 in saline was given in a primary injection and each of two booster injections.

B. Preparation of Hybridomas

The non-secreting SP2/0-AG14 BALB/c myeloma cell line (ATCC No. CRL-1581, American Type Culture Collection, Rockville, Md.) (Shulman, M., C. D. Wilde and G. Kohler, *Nature*, vol. 276, (1978), p. 269) was provided by Dr. S. Robertson, Department of Microbiology, University of Texas Health Science Center, Dallas, Tex. Spleen cells from immunized mice and myeloma cells were washed separately in serum-free medium and then combined in a 7:1 ratio, respectively. Following a ten minute centrifugation at 400$\times$g, the supernatant was decanted and all residual fluid carefully removed with sterile swabs. Cell fusion was initiated by the dropwise addition of 1 ml pre-warmed (37° C.) 50% polyethylene glycol (PEG 1500; American Type Culture Collection, Rockville, MD) over a one minute period. Cells were gently stirred for one minute, and 2 ml pre-warmed serum-free medium were added dropwise over the next two minutes. Finally, 7 ml of pre-warmed Dulbecco's Modified Eagle's Medium (DME; M. A. Bioproducts, Walkersville, MD) supplemented with 20% fetal bovine serum (FBS; M. A. Bioproducts, Walkersville, MD) were slowly added over the next two and one-half minutes.

The cells were centrifuged at 400$\times$g for ten minutes and the pellet gently resuspended to a final concentration of 2$\times$10$^6$ cells/ml in complete DME (see Kennett, R. H., In: R. H. Kennett, T. J. McKearn and K. B. Bechtol, eds. (New York, Plenum Press, 1980) p. 365) supplemented with 3$\times$10$^{-6}$M glycine. 50 $\mu$l of this suspension was aliquoted into each well of a 96-well microtiter tissue culture plate (Bellco, Vineland, NJ) containing 1$\times$10$^5$ normal BALB/c spleen feeder cells per well in 50 $\mu$l of complete DME. One day after fusion, 100 microliters of complete DME supplemented with 2$\times$ hypoxanthine, thymidine and aminopterin were added to each well. Plates were incubated at 37° C. in 7% CO$_2$ for 7-10 days prior to screening for anti-*M. pneumoniae* activity by ELISA. Following positive identification by ELISA, hybrid cells were cloned by limited dilution in 96-well microtiter tissue culture plates containing 1$\times$10$^5$ BALB/c spleen feeder cells per well.

Cloned hybridomas were grown in ascites in BALB/c (6-10 week old mice). Mice were injected i.p. with 0.5 ml Pristane ® (2,6,10,14-tetramethylpentadecane, Aldrich Chemical Co., Milwaukee, Wis.) on days 1 and 4. Five to ten days later, the mice were given an i.p. injection of 1$\times$10$^6$ hybridoma cells in saline. Seven to ten days later, the ascites fluid was tapped from the peritoneal cavity.

EXAMPLE II. Screening of Hybridomas for Monoclonal Antibodies Specific for *M. pneumoniae* Determinants

A. Purification of lipid determinants

Prerequisite to the screening of the hybridomas for their specificity for *M. pneumoniae* determinants was a method for the purification of the determinants themselves. Lipid *M. pneumoniae* antigens for use in the analysis of the specificity of the monoclonal antibodies produced by the hybridomas were purified as follows. Lipids were extracted from *M. pneumoniae* B16 strain according to the procedure of Bligh, E. G. and W. J. Dyer. *Can. J. Biochem. Physiol.*, vol. 37 (1959), p. 911. The methanol phase was re-extracted a total of four times. Pooled chloroform phases containing mycoplasma lipids were evaporated by vacuum distillation under nitrogen and weighed The methanol phase contaning mycoplasma proteins was centrifuged at 45,000$\times$g, the supernatant decanted, and the pellet resolubilized in carbonate buffer (1.6 g Na$_2$CO$_3$+2.94 g NaHCO$_3$+0.2 g NaN$_3$ per liter of H$_2$O, pH 9.6) at 200 ng protein per 50 $\mu$l per well for antigen attachment. Samples of the lipid and protein phases were analyzed for protein content using SDS-PAGE and the silver staining method of Oakley, B. R., D. R. Kirsch and N. R. Norris. *Anal. Biochem.*, vol. 105 (1980), p. 361.

Before TLC fractionation, phosphorus content of the lipid extracts was calculated according to the method of Bartlett, G. R., *J. Biol. Chem.*, vol. 234 (1959), p. 466. This procedure allowed for estimation of the phospholipid content of the sample and prevented overloading of the silica gel plates. Prior to loading, 20$\times$20 cm Woelm Silica Gel G plates (1,000 micron, Analtech, Inc., Newark, Del.), were washed with a neutral developing solvent consisting of chloroform, methanol and water (65:35:6). Mycoplasma lipids were resuspended in 1.0 ml chloroform-methanol (1:1) and spotted across the gel.

Following chromatographic separation of the lipids in a neutral solvent system, the resulting fractions were detected with ultraviolet light by spraying with 1 mM TNS (6(p-toluidino)-2-napthalene sulfonic acid, potassium salt, Aldrich Chemical Co., Milwaukee, Wis.) in 50 mM Tris base, pH 7.5. Fluorescent bands were scraped and suspended overnight in 10 ml chloroform-methanol-water (5:10:4). The chloroform-methanol-water phases were separated from the denser silica gel phase and placed in a centrifuge tube. The mixture was vortexed, centrifuged at 250$\times$g for 3 minutes and the lower chloroform phase was collected. Any remaining lipid in the silica gel suspension was re-extracted with 2 ml of the above solution. The mixture was vortexed, centrifuged as before and the lower chloroform phase collected. This process was repeated once more, and all three chloroform phases were pooled and evaporated by vacuum distillation.

Lipid bands were analyzed by spraying with periodate-Schiff reagent, ninhydrin spray reagent, molybdate spray reagent and by sulfuric acid charring (Randerath, K., *Thin-Layer Chromatography*. New York, Academic Press, 1963, p. 136). Seven lipid bands were detected. Control standards for TLC included sphingomyelin, phosphatidylcholine, phosphatidylethanolamine, lysolecithin, diglyceride, phosphatidylinositol and phosphatidylacetate. Two of the bands were identified as comigrating with sphingomyelin and phosphatidylcholine. Those same two bands and one other reacted strongly with the molybdate spray, indicating the presence of phospholipids. Glycolipids were identified in three of the fractions by their strong reaction with periodate-Schiff reagent. No amines were detected in any of the fractions by ninhydrin spray reagent.

The antigens resulting from extraction and purification according to these procedures are as follows:

(1) a whole lipid extract consisting of the lipid material obtained from pooling chloroform phases following the initial extraction of *M. pneumoniae;*

(2) a protein preparation collected from the methanol-water phase; and (3) fractions 3-7 isolated following chloroform-methanol water extraction of each fraction from TLC of the whole lipid extract.

Protein antigens were also purified according to the method of Example III, described below.

B. Attachment of protein and lipid determinants to PVC matrix

Attachment of lipid extracts or TLC-fractionated lipids to PVC microtiter wells was accomplished by suspension of the lipid extracts in a minimal volume of 0.2 ml of chloroform. To this mixture was added 1.8 ml of methanol. Antigen dilutions (1:5 for whole lipids and 1:10 for TLC-fractionated lipids) were made with 95% ethanol. Fifty microliters of the diluted lipids were distributed into each microtiter well. Suspensions were then air dried at 37° C. and stored under desiccant at 4° C.

Proteins were bound to the PVC microtiter test wells as follows. Affinity column-purified mycoplasma protein was incubated overnight at 4° C. in a high pH coating buffer (1.6 g $Na_2CO_3$+2.94 g $NaHCO_3$+0.2 g $NaN_3$ per liter of $H_2O$, pH 9.6) in the PVC microtiter test wells. Excess protein was aspirated and the matrix washed once with PBS. The protein pellets collected from the methanol-water phase of *M. pneumoniae* were attached to the PVC microtiter test wells by the same method.

C. Screening Hybridomas with Purified Antigens

A modified enzyme-linked immunosorbent assay (ELISA) (Voller, A., D. Bidwell and A. Bartlett. In: N. R. Rose and H. Friedman, eds., Manual of Clinical Immunology (Washington, D.C., American Society for Microbiology), (1976) p. 506) was used to screen hybridomas for the ability to produce antibodies to *M. pneumoniae* organisms, whole lipid extracts, protein extracts, and TLC-fractionated lipids. Briefly, after antigen coating of PVC microtiter plates according to the above method, wells were filled with PBS supplemented with 1% bovine serum albumin (BSA) (PBS-BSA) and incubated for 2 hours at 37° C. Plates were then washed three times with PBS. Fifty microliters of test serum diluted with PBS-BSA, monoclonal antibody supernatant (undiluted), or PBS-BSA (for a control value) were added to the designated wells. Following a 2 hour incubation at 25° C. for test serum or an overnight incubation at 4° C. for hybridoma supernatants, wells were washed four times with PBS. Fifty microliter aliquots of alkaline phosphatase conjugated sheep antimouse Ig (New England Nuclear, Boston, MA) diluted 1:1000 in PBS-BSA were then added to each well. Plates were incubated for 2 hours at 37° C., followed by sequential washing with PBS (three times) and distilled $H_2O$ (twice). Finally, 50 µl of 1 mg disodium p-nitrophenyl phosphate (pnp, Sigma Chemical Co., St. Louis, MO) per ml, prepared in diethanolamine buffer (see Voller, 1976), were added to each well and the wells incubated for 30 minutes at 37° C. Antibody reactivity was measured by optical density readings at 405 nm using a microELISA Reader (Dynatech).

Of the 936 wells showing positive growth, 293 wells were reactive to *M. pneumoniae* (ELISA values greater than or equal to 0.150). One hundred fifty two of those 293 clones were selected for screening against chloroform-methanol-water extracted lipid and protein antigens. Of these clones, 35.5% were non-reactive to both preparations (ELISA values less than or equal to 0.100), 13.2% were equally reactive to both antigen preparations, and 51.3% were predominantly reactive to lipids.

Monoclonal antibodies were also isotyped by ELISA. Antigen-coated microtiter wells were first exposed to PBS-BSA and then to monoclonal antibody (undiluted culture supernatants) as previously described. After a 2 hour incubation, wells were washed four times with PBS. Rabbit anti-mouse IgG1, IgG2a, IgG3, IgM, and IgA (available from Miles Laboratories, Elkhart, IN) were diluted 1:8 in PBS-BSA, and 50 µl were added to designated wells. Wells were incubated for 2 hours at 37° C. followed by 4 washed with PBS. Fifty microliter aliquots of alkaline phosphatase conjugated goat anti-rabbit Ig (Miles, diluted 1:1000 in PBS-BSA) were added to each well. Plates were incubated for 2 hours at 37° C., followed by sequential washing with PBS (three times) and distilled $H_2O$ (twice). Wells were exposed to pnp as previously described and optical density readings measured at 405 nm.

Some representative clones are listed, along with their isotype, in Table 1. As can be seen, some of the clones produced monoclonal antibodies specific for both protein and lipid determinants of *M. pneumoniae*, others were specific for only lipid determinants, and others were specific for only protein determinants. For each clone, a control was run for reactivity to PBS. In all cases, the controls were less than or equal to 0.002. The values represent the mean and standard deviation of triplicate samples.

EXAMPLE III. Purification of *M. pneumonie* Protein P1 Using Monoclonal Antibodies Against P1

The purification of *M. pneumoniae* protein P1 with monoclonal antibodies against P1 bound to an insoluble support system was accomplished in several steps as follows. The first step in this purification was to identify hybrid clones producing anti-P1 antibody by whole cell radioimmunoprecipitation (RIP) assay, as follows.

[$^{35}$S]methionine-labeled *M. pneumoniae* were suspended in cold PBS and 125 microliter aliquots of this suspension were mixed with 40 microliters of test antisera. The suspensions were placed on a rocker platform for 90 minutes at 4° C. to allow antibody binding to accessible mycroplasma surface proteins. The mycroplasmas were pelleted in a Microfuge B (Beckman Instruments, Inc., Palo Alto, Ca.) and washed once with PBS to remove unabsorbed antibody. The organisms were resuspended in 1.0 ml TDSET

TABLE 1

Reactivity of Monoclonal Antibodies To Lipid And Protein Extracts of *M. Pneumoniae*

| Clone | Lipid | Protein | Isotype |
|---|---|---|---|
| 5B$_{12}$ | .245 ± .005$^a$ | .226 ± .045 | Not Tested |
| 8E$_5$ | .270 ± .041 | .219 ± .077 | Not Tested |
| 11H$_{12}$ | .263 ± .072 | .285 ± .023 | Not Tested |
| 2G$_2$ (ATCC HB 8972) | .690 ± .023 | .058 ± .006 | IgG3 |
| 3B$_3$ (ATCC HB 8973) | .694 ± .122 | .058 ± .031 | IgG3 |
| 17D$_4$ | .770 ± .082 | .069 ± .053 | IgG3 |
| 17H$_9$ | .581 ± .165 | .064 ± .024 | IgG3 |
| 11F$_{10}$ | 1.218 ± .086 | .177 ± .111 | IgG3 |
| 16H$_8$ | 1.006 ± .045 | .241 ± .001 | IgG3 |
| 3B$_{11}$ | .344 ± .002 | .060 ± .033 | IgM |
| 4H$_2$ | .582 ± .052 | .088 ± .038 | IgM |
| 11A$_8$ | .821 ± .045 | .179 ± .026 | IgM |
| 16A$_3$ | .378 ± .081 | .052 ± .061 | IgM |
| 8G$_4$ | .636 ± .047 | A | IgA |
| 10G$_7$ | .389 ± .005 | A | IgA |
| 2D$_{11}$ | .512 ± .004 | A | IgA |

A = Tested by radioimmunoprecipitation (RIP), results negative (10 mM Tris-HCl (pH 7.8), 0.2% (wt/vol) sodium deoxycholate (DOC), 0.1% (wt/vol) sodium dodecyl sulfate (SDS), 10 mM EDTA, and 1% (vol/vol) Triton X-100) that contained 100 mM phenylmethylsulfonylfluoride), vortexed, and incubated at 37° C. for 1 hour with periodic vortexing to ensure efficient solubilization. Insoluble material was removed by centrifugation at 45,000×g for 1 hour.

The uppermost 0.9 ml of supernatant was carefully transferred to another tube, and 250 μl of washed *Staphylococcus aureus* (Staph A) were added to each supernatant. The suspensions were placed on a rocker platform and incubated for 90 minutes at 4° C. The Staph A was washed four times with TDSET, and adsorbed *M. pneumoniae* surface immunogens were eluted in 35 μl of SP buffer (0.1M Tris-HCl (pH 6.8), 2% (wt/vol) SDS, 20% (vol/vol) glycerol, 2% (wt/vol) β-mercaptoethanol and 0.02% (wt/vol) bromophenol blue). The Staph A was pelleted and the supernatant subjected to one-dimensional SDS-polyacrylamide gel electrophoresis (SDS-PAGE) according to the method of Laemmli, U. K. "Cleavage of Structural Proteins During the Assembly of the Head of Bacteriophage T4." *Nature (Lond.)*, vol. 227 (1970), p. 680 using a 1.5 mm slab consisting of a 3% stacking and a 7.5% separating gel. Upon completion of electrophoresis, the slab was placed in fixative (methanol/acetic acid/H$_2$O, 45:10:45) overnight. The gel was then processed for fluorography according to the method of Bonner, W. M. and R. A. Laskey. "A Film Detection Method for Tritium-Labeled Proteins and Nucleic Acids, in Polyacrylamide Gels." *Eur. J. Biochem.*, vol. 46 (1974), p. 83.

Anti-P1 monoclonal antibodies which bound to protein A-bearing formalinized Staph A were expanded by ascitic growth in mice. These included monoclonals from clones H5.2G$_4$ (ATCC HB 8419) and H13.6E$_7$ (ATCC HB 8420). Drawn ascites fluid was centrifuged at 1,000×g for 10 minutes to remove cells, then diluted in 0.1M phosphate buffer (pH 7.2) and applied to a protein A-Sepharose (Sigma Chemical Co., St. Louis, Mo.) column. Unbound material was washed through the column with phosphate buffer, and IgG monoclonal antibodies were eluted with 1M acetic acid. Four antibody-containing fractions (determined spectrophotometrically at A$_{280}$) were pooled in equal proportions, neutralized and concentrated by negative pressure dialysis.

The antibodies were then coupled to cyanogen bromide-activated Sepharose 4B which had previously been loaded into a chromatography column, washed with 1 mM HCl and equilibrated in coupling buffer. The coupling reaction was carried out on a gyratory shaker at room temperature for two hours. Unreacted IgG was washed from the coupled gel, and excess reactive groups were blocked with 0.1M Tris buffer (pH 7.5). The coupled gel was then washed sequentially with coupling buffer (0.1M acetate (pH 4) containing 0.5M NaCl), 0.1M Tris (pH 7.5) containing 0.15M NaCl, and TDSET, resulting in an anti-P1 column.

The anti-P1 column was then used to purify surface protein P1 as follows. *M. pneumoniae* were solubulized in TDSET containing 1 mM phenylmethylsulfonylflouride (PMSF) and centrifuged at 100,000×g for 45 minutes on a cushion of TDSET containing 5% sucrose in TDSET to remove insoluble debris. The TDSET-soluble [$^{35}$S]methionine-labeled *M. pneumoniae* preparation was then applied to the anti-P1 affinity column and the column washed with TDSET until the radioactivity in the wash buffer decreased to background levels. Bound P1 protein was eluted with 50% (vol/vol) ethylene glycol (pH 11.5), neutralized and concentrated by vacuum dialysis against Tris-saline (pH 8.2) containing 0.1% DOC.

Aliquots from unbound and bound labeled peaks were analyzed by SDS-PAGE by adding them to SDS-PAGE sample preparation buffer, electrophoresing on 7.5% acrylamide gels and processing for fluorography. Analysis revealed a single eluted protein which co-migrated with protein P1.

EXAMPLE IV. Diagnosis of Primary Atypical Pneumonia Using Monoclonal Antibodies Against *M. pneumoniae* Protein P1

Monoclonal antibodies against *M. pneumoniae* protein P1 were used to detect the presence of protein P1 in human body fluids as follows. Due to the unavailability of actual samples from individuals suffering from mycoplasma pneumonia, samples were simulated by diluting whole *M. pneumoniae* in sputum samples from normal individuals. As a control, whole *M. pneumoniae* were dissolved in PBS and aliquoted at 5 μg/75 μl into each microtiter test well, air-dried at 37° C., then fixed with 95% ethanol.

Simulated sputum samples were prepared as follows. *M. pneumoniae* were solubilized in SDS Triton X-PMSF, at approximately 500 μg/ml (1:2 dilution) and 100 μg/ml (1:10 dilution). The final *M. pneumoniae* protein content of each microtiter test well was 1.5 μg per well at the 1:2 dilution and 0.3 μg per well at the 1:10 dilution. Diluted *M. pneumoniae* were then mixed with sputum and fixing using 95% ethanol.

The protein A-sepharose affinity column described in Example III above was used to purify monoclonal antibodies specific for surface adhesin P1. A pool of monoclonal antibodies obtained from hybridomas H10.8$E_8$, H1.25$B_8$, H12.21$B_8$, H13.6$E_7$ (ATCC 8420) and H5.2$G_4$ (ATCC HB 8419), concentrated at 2.8 mg/ml and used at 50 μl per well. Monoclonal antibodies were diluted in PBS+1% BSA. The results of this diagnostic test are summarized in Table 2 as follows. Each number respresents the mean and standard deviation from quadruplicate samples minus the sputum control background.

TABLE 2

Detection of *M. pneumoniae* Protein P1 Antigens in Sputum

| Antigen (dilution) | Concentration of Monoclonal Antibodies Purified from Hybridomas H10.8$E_8$, H12.5$B_8$, H12.21$B_8$, H5.2$G_4$ & H13.6$E_7$ (1:50) | (1:1000) | (1:5000) |
|---|---|---|---|
| Sputum (1:10) + *M. pneumoniae* (1:2) | .466 ± .090 | .329 ± .024 | .106 ± .008 |
| Sputum (1:10) + *M. pneumoniae* (1:10) | .164 ± .050 | .032 ± .030 | .021 ± .008 |
| Whole *M. pneumoniae* 5 μg/well | .668 ± .055 | .952 ± .142 | .883 ± .149 |

EXAMPLE V. Diagnosis of Primary Atypical Pneumonia Using Monoclonal Antibodies Against Lipid Determinants of *M. pneumoniae*

Monoclonal antibodies specific for lipid antigens of *M. pneumoniae* were used to detect the presence of *M. pneumoniae* in body fluids by the following method. Simulated sputum samples were pepared as summarized in Example IV above and fixed to PVC microtiter test wells using 95% ethanol. The monoclonal antibodies utilized were those secreted by the hybridomas H13.2$G_2$ (ATCC HB 8424), H13.17$H_9$, (ATCC HB8972), H13.11$F_{10}$ (ATCC HB 8425), and H13.16$H_8$. The results are summarized in Table 3 as follows. Each number represents the mean and standard deviation from quadruplicate samples minus the sputum control background.

TABLE 3

Detection of *M. pneumoniae* Lipid Antigens in Sputum

| Antigen (dilution) | Antibody: Pool of Monoclonal Antibodies from hybridomas H13.2$G_2$, H13.17$H_9$, H13.11$F_{10}$, H13.16$H_8$ | H13.17$H_9$ | H13.3$B_3$ (ATCCHB8972) |
|---|---|---|---|
| Sputum (1:10) + *M. pneumoniae* (1:2) | .841 ± .050 | .124 ± .019 | .331 ± .040 |
| Sputum (1:10) + *M. pneumoniae* (1:10) | .795 ± .019 | .075 ± .018 | .304 ± .023 |
| Whole *M. pneumoniae* 5 μg/well | 1.063 ± .016 | .984 ± .105 | 1.165 ± .102 |

EXAMPLE VI. Diagnosis of Primary Atypical Pneumonia Using Monoclonal Antibodies Specific for *M. pneumoniae* Protein Determinants Other than P1

As noted, detection of protein antigens of *M. pneumoniae* other than P1 may be used as a check on the diagnosis by monoclonal binding to P1 and to confer additional specificity to the analysis of the immune response to mycroplasma infection. However, the humoral response of the mice injected with wild-type virulent *M. pneumoniae* B16 strain organisms was restricted in that 64% of the monoclonal antibodies produced by injection with this strain was directed against the surface protein P1. Because of this dominance of P1, when whole *M. pneumoniae* was used as the antigen to prime an animal to produce antibody-producing cells which produce antibodies specific for the antigens of *M. pneumoniae*, it was necessary to "unmask" the other, non-immunodominant, protein antigens of *M. pneumoniae.* Among these non-immunodominant proteins are the proteins identified by Applicant as proteins with molecular weights of 215,000, 210,000 (designated HMW 2), 140,000 (designated HMW 3), 135,000 (designated P4), 110,000 (designated P2), 85,000, 72,000, and 37,000 (see Krause, et al., *Inf. Immun.*, vol. 35, pp. 809–817 and Krause, et al., *Inf. Immun.*, vol. 37, pp. 382–386, both incorporated by reference). Other non-immunodominant proteins of *M. pneumoniae* are listed in Table 4. Indicates are that one or more of these protein components of *M. pneumoniae* may themselves be dominant over the others, nevertheless, in order to raise monoclonal antibodies specific for any of these proteins, the following procedure was utilized.

BALB/c female mice (3–6 weeks old) were injected with 100 μg of wild-type *M. pneumoniae* emulsified in FCA i.p. Fourteen days later, the mice were given an i.p. boost of 100 μg wild-type *M. pneumoniae* emulsified in FIA. Three days before fusing, the class IV $HA^-$avirulent mutant *M. pneumoniae* (ATCC 39505), deficient in its ability to produce the immunodominant protein P1, was injected both i.p. (100 μg emulsified in FCA) and i.v. (100 μg in saline). When fused with myeloma cells as described above, a number of monoclonals resulted, and only one of the 61 resulting hybridomas secreted antibody against P1. Examples of the proteins (non-P1 clones) recognized by the monoclonal antibodies secreted by those hybridomas are shown by their molecular weight, along with the isotype of the monoclonal antibodies produced, in Table 4.

These monoclonal antibodies specific for *M. pneumoniae* protein antigens other than P1 were used in a method for the detection of *M. pneumoniae* in body fluids as follows. Sputum samples were simulated as described in Example IV above. Monoclonal antibodies from hybridoma H13.4$F_4$ were purified by affinity-column purification as described in Example III above. This monoclonal antibody is specific for a 32K dalton molecular weight protein antigen. Fifty microliters of monoclonal antibody were aliquoted into each microliter test well and the concentration of the antibody was approximately 100 μg/ml. Also, pooled monoclonal antibodies from the hybridomas H13.1$C_8$ and H17.5$C_4$ (not listed in Table 4), specific for a 29K dalton molecular weight antigen and a 110K dalton molecular weight antigen, respectively, were also purified by affinity-column purification and then used to detect *M. pneumoniae.* The monoclonal antibodies were used at a concentration of approximately 100 μm/ml, and 50 μl of the pooled monoclonal antibodies were aliquoted into each well. The results are summarized in Table 5 as follows. Each number represents the mean and standard deviation

TABLE 4

Representative Monoclonal Antibodies to *Mycoplasma pneumoniae* Proteins

| Molecular Weight of Protein Antigen | Number of Clones | Representative Clone | Representative Isotype |
|---|---|---|---|
| 32K | 6 | H13.4F4(ATCC HB8974) | IgG$_1$ |
|  |  | H13.14D4 | IgM |
| 110K (P$_2$) | 1 | H17.8A5 (ATCC HB 8423) | N.D. |
| 127K | 2 | H13.7H$_{11}$ | IgM |
|  |  | H13.6E7 (ATCC HB 8420) | IgG$_{2a}$ |
| 165K (P$_1$) | 8 | H5.3F5 | IgG$_1$ |
|  |  | H5.2G4 (ATCC HB 8419) | IgG$_{2a}$ |
|  |  | H12.24G6 | IgG$_{2b}$ |
| 200K | 3 | H13.1B2 | IgG$_1$ |
|  |  | H13.1D$_{11}$ (ATCC HB 8422) | IgG$_3$ |
|  |  | H13.18H7 | IgM |
| 28,25K | 1 | H13.16F$_{10}$ | IgG$_{2b}$ |
| 72,42K | 1 | H13.14E7 | IgM |
| 127,42K | 1 | H13.22C9 | IgG$_{2b}$ |
| 155,42K | 2 | H13.18E7 | IgM |
| 120,55K | 1 | H13.4G4 | IgM |
| 155,42,30K | 7 | H13.9G4 (ATCC HB 8421) | IgG |
|  |  | H13.7G$_1$ | IgM | from quadruplicate samples minus the sputum control background.

TABLE 5

Detection of *M. pneumoniae* Antigens uz,7/26 Other Than P1 in Sputum

| Antigen (dilution) | H13.4F4 (ATCC8974) | H13.1C8 + H17.5C4 |
|---|---|---|
| Sputum (1:10) + *M. pneumoniae* (1:2) | .102 ± .004 | .281 ± .060 |
| Sputum (1:10) + *M. pneumoniae* (1:10) | .036 ± .003 | .189 ± .056 |
| Whole *M. pneumoniae* 5 µg/well | .648 ± .083 | .050 ± .030 |

It will be recognized by those skilled in the art who have the benefit of this disclosure that a number of variations of the above examples may be utilized to similar advantage. For instance, antigen-antibody reactivity can be measured with methods other than ELISA, for instance, a radioimmunoassay (RIA) or radioimmunoprecipitation (RIP) test could be utilized. It is expected that these and other modifications of the present invention will be considered to be within the spirit and scope of the invention which is limited only by reference to the following claims.

Deposits according to the invention were submitted to the American Type Culture Collection (ATCC) Rockville, Md. 20852. The following deposits were accorded the corresponding ATCC designations.

| Deposit | ATCC Designation |
|---|---|
| H5.2G4 | HB8419 |
| H13.6E7 | HB8420 |
| H13.9G4 | HB8421 |
| H13.1D$_1$1 | HB8422 |
| H17.8A5 | HB8423 |
| H13.2G2 | HB8424 |
| H13.11F$_1$0 | HB8425 |
| Mutant 22 | 39505 |
| H13.3B3 (or 3B3) | HB8972 |
| H13.17D4 (or 17D4) | HB8973 |
| H13.4F4 | HB8974 |

What is claimed is:

1. The hybridoma that produces the monoclonal antibody specific for a non-immunodominant protein antigen of *Mycoplasma pneumoniae*, said hybridoma being a clone selected from the group consisting of: clone H13.9G4 (ATCC HB8421); clone H13.1D$_{11}$(ATCC HB8422); clone H17.8A5(ATCC HB8423) and clone H13.4F4( ATCC HB8974).

2. The monoclonal antibody specific for a non-immunodominant protein antigen of *Mycoplasma pneumoniae* said monoclonal antibody being produced by a hybridoma clone selected from the group consisting of: clone H13.9G4 (ATCC HB8421); clone H13.1D$_{11}$(ATCC HB8422); clone H17.8A5(ATCC HB8423) and cone H13.4F4(ATCC HB8974).

3. A method for the immunochemical diagnosis of *Mycoplasma pneumoniae* infection in a mammal using a monoclonal antibody comprising:
   contacting body fluid from said mammal with a monoclonal specific for a non-immunodominant protein antigen of *Mycoplasma pneumoniae;*
   measuring the amount of material immunologically bound by said monoclonal antibody; and
   determining by comparing, for a positive diagnosis, whether the amount of bound material is greater than that found with body fluid from an uninfected mammal.

4. A hybridoma that produces the monoclonal antibody specific for a lipid antigen of *Mycoplasma pneumoniae* said hybridoma being a clone selected from the group consisting of: clone H13.2G2(ATCC HB8424); clone H13.11F$_{10}$(ATCC HB8425); clone H13.17D4(ATCC HB8973) and clone H13.3B3(ATCC HB8972).

5. The monoclonal antibody specific for a lipid antigen of *Mycoplasma pneumoniae*, said monoclonal antibody being produced by a hybridoma clone selected from the group consisting of: clone H13.2G2(ATCC HB8424); clone H13.11F$_{10}$(ATCC HB8425); clone H13.17D4(ATCC HB8973) and clone H13.3B3(ATCC HB8972).

6. A method for the immunochemical diagnosis of *Mycoplasma pneumoniae* infection in a mammal, comprising:
   contacting a body fluid from said mammal with monoclonal antibody specific for a lipid antigen of *Mycoplasma pneumoniae;*
   measuring the amount of material immunologically bound by said monoclonal antibody; and
   determining by comparing, for a positive diagnosis, whether the amount of bound material is greater than that found with body fluid from an uninfected mammal.

7. A method for the immunochemical diagnosis of *Mycoplasma pneumoniae* infection in a mammal as set forth in claim 6, wherein said monoclonal antibody is produced by a hybridoma clone selected from the group consisting of: clone H13.2G2(ATCC HB8424); clone H13.11F$_{10}$(ATCC HB8425); clone $H13.17D_4$(ATCC HB8973) and clone $H13.3B_3$(ATCC HB8972).

8. A method for producing a monoclonal antibody specific for a non-immunodominant antigen of a microorganism comprising:

injecting into an animal one or more doses of a microorganism which is *Mycoplasma pneumoniae* over a period of time in amounts and at a frequency sufficient to induce an immune response;

selecting a mutant strain of the same microorganism deficient in its ability to produce an immunodominant antigen;

injecting one or more doses of said mutant microorganism into said animal prior to recovering antibody-producing cells from said animal, said doses of the mutant microorganism being injected in amounts and at a frequency sufficient to induce an immune response to non-immunodominant antigens;

recovering cells from said animal that produce antibodies immunoreactive with said microorganisms;

forming hybridomas by fusing said cells with myeloma cells;

culturing said hybridomas;

selecting a hybridoma that produces an antibody specific for a non-immunodominant antigen of said microorganism as a product of said hybridoma, provided however that when said microorganism is *Mycoplasma pneumoniae* said non-immunodominant antigen is not *Mycoplasma pneumoniae* protein P1; and culturing that selected hybridoma.

9. The method of claim 8 wherein said mutant microorganism is the class IV $HA^-$ mutant *M. pneumoniae* (ATCC 39505).

10. The method of claim 9, wherein a monoclonal antibody specific for a non-immunodominant protein antigen of *Mycoplasma pneumoniae* is produced.

11. The method of claim 8, wherein a monoclonal antibody specific for a lipid antigen of *Mycoplasma pneumoniae* is produced.

* * * * *